United States Patent [19]

Bechtold, Jr.

[11] 4,182,040
[45] Jan. 8, 1980

[54] ENDODONTIC FILE HOLDER AND GAUGE

[76] Inventor: Edmund C. Bechtold, Jr., 1630 SW. Clay St., Portland, Oreg. 97201

[21] Appl. No.: 879,240

[22] Filed: Feb. 21, 1978

[51] Int. Cl.² .............................................. A61C 3/00
[52] U.S. Cl. ........................................ 433/77; 433/75
[58] Field of Search ................................... 32/57, 40 R

[56] References Cited

U.S. PATENT DOCUMENTS

| 3,905,375 | 9/1975 | Toyama | 32/57 |
|---|---|---|---|
| 3,938,253 | 2/1976 | Barnard | 32/57 |

Primary Examiner—Robert Peshock
Attorney, Agent, or Firm—Oliver D. Olson

[57] ABSTRACT

Endodontic files extend freely through openings in a gauge plate supported through a central threaded opening by an elongated, rotatable screw extending upwardly from a base. A post extends upwardly from the base and slidably engages the gauge plate to prevent rotation of the plate while allowing it to move vertically relative to the base upon rotation of the screw, whereby to afford adjustment of the vertical distance between the base and gauge plate to correspond with the depth of radicular pulp to be removed from the root canal of a tooth. Depth stoppers on the files are adjusted along the length of the files to bring them into abutment with the upper surface of the gauge plate, thereby establishing the depth to which the files are to penetrate the root canal. A cover fits removably over the gauge plate and base to retain the files on the gauge plate during transport and to accommodate autoclaving and sterile storage.

5 Claims, 3 Drawing Figures

ENDODONTIC FILE HOLDER AND GAUGE

BACKGROUND OF THE INVENTION

This invention relates to endodontic files, and more particularly to a novel holder and gauge by which such files may be adjusted precisely to desired working length, displayed for use and retained for autoclaving and sterile storage.

It is the general practice among dentists to store endodontic files in a case from which those to be used are removed and the depth stoppers adjusted one at a time to desired working length and, after use, to clean the files and return them to the storage case.

The only prior endodontic file holder and gauge known to applicant consists of a base supporting an upstanding fixed post which slidably receives a gauge plate for manual vertical adjustment, and a set screw releasably interengaging the plate and post for securing the plate in adjusted position. Although adjustment of the gauge plate is faster than the manual adjustment of each file, precise adjustment of the gauge plate is as difficult to achieve as is precise manual adjustment of the working length of each file. Moreover, the files are exposed to contamination during storage and are subject to being spilled from the holder if the latter is tipped over or otherwise jostled during transport.

SUMMARY OF THE INVENTION

In its basic concept, this invention provides an endodontic file holder and gauge in which a file-holding gauge plate is supported by a rotary screw for precise vertical adjustment relative to an underlying base, and a cover removably encloses the guage plate and supported files.

It is by virtue of the foregoing basic concept that the principal objective of this invention is achieved; namely, to overcome the aforementioned disadvantages and limitations of prior methods and means for adjusting and storing endodontic files.

Another objective of this invention is the provision of an endodontic file holder and gauge of the class described in which a portion of the gauge plate is provided with a plurality of steps each providing a different gauging surface for adjusting endodontic files to different working lengths for use in flaring a root canal.

A further objective of this invention is the provision of an endodontic file holder and gauge of the class described in which a cover is adjustable between a position spaced upwardly from the base to facilitate autoclaving of used files and a position engaging the base to provide sterile storage for the cleaned files.

Still another objective of this invention is the provision of an endodontic file holder and gauge of the class described which is of simplified construction for economical manufacture.

The foregoing and other objects and advantages of this invention will appear from the following detailed description, taken in connection with the accompanying drawings of a preferred embodiment.

DESCRIPTION OF THE PREFERRED EMBODIMENT

Figure 3:
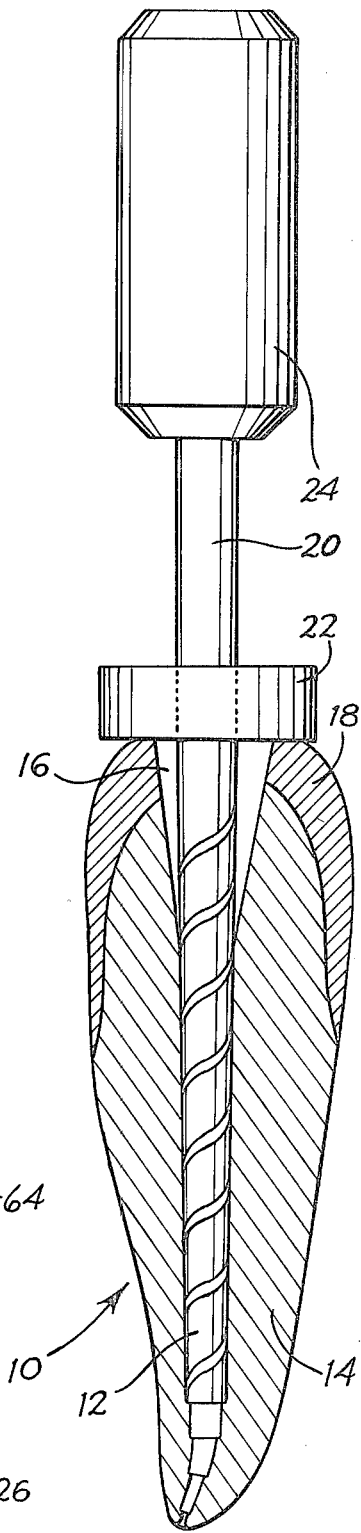
FIG. 3 is a vertical section through an incisor tooth showing an endodontic file in operative position, the combination being illustrated on an enlarged scale approximately ten times actual scale.

Referring first to FIG. 3 of the drawings, an incisor tooth 10 is shown in cross section to illustrate a root canal 12 extending upwardly from the apex to the upper portion of the dentin 14 where it communicates with a tapered access opening 16 provided by drilling inward through the enamel 18 and dentin of the crown.

As is well known, root canal treatment involves the removal of radicular pulp from the root canal, by use of a plurality of tiny files 20 of varying sizes and working lengths, the latter being determined from radiographs of the tooth being treated.

In the treatment, a number of files of equal working length but progressively larger in size are extended to the full depth of the canal and worked in appropriate manner to remove the pulp. Since the canal increases in diameter outwardly from the apex, a series of progressively larger files of progressively shorter working lengths then are worked in the canal to complete the pulp removal. FIG. 3 illustrates the stepped arrangement resulting from this latter procedure which is terminated with the largest size file of shortest working length shown in place of FIG. 3.

It is also well known that the desired working length of each file is estabished by means of a depth stopper 22, usually in the form of a resilient rubber washer, mounted frictionally on the file for adjustment along the length thereof to the desired position as determined from radiographs of the tooth. As indicated hereinbefore, adjustment of the working lengths of files conventionally is accomplished by the use of a ruler and manually adjusting the depth stopper along the length of each file, with the final series of files being shortened progressively by one millimeter increments.

Each file is provided at its outer end with an enlarged handle 24 for facilitating its manual manipulation by the fingers, as is well known.

Figure 2:
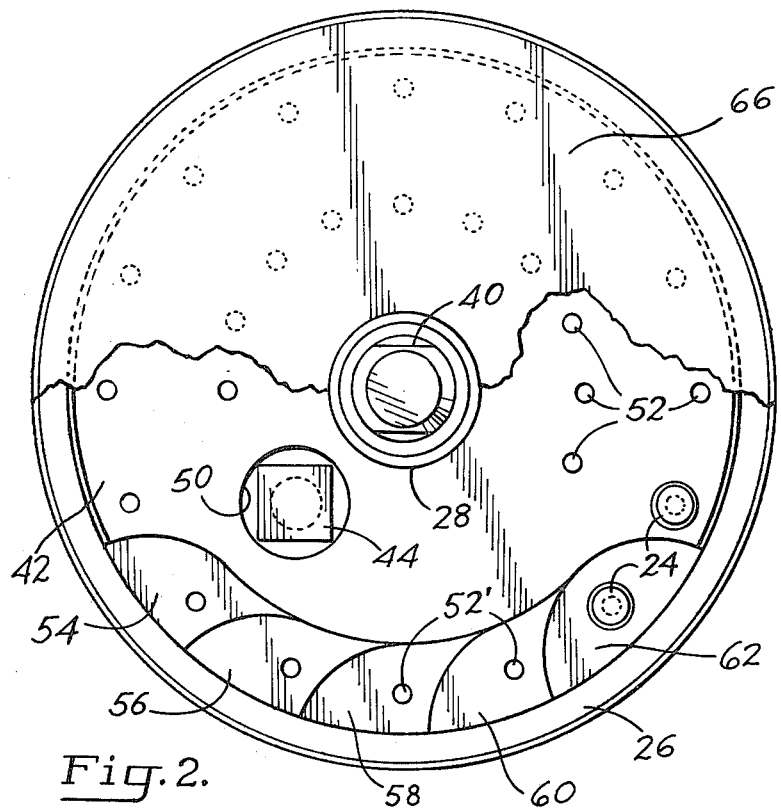
FIG. 2 is a plan view as viewed from the top in FIG. 1, a portion of the cover being broken away.
Figure 1:
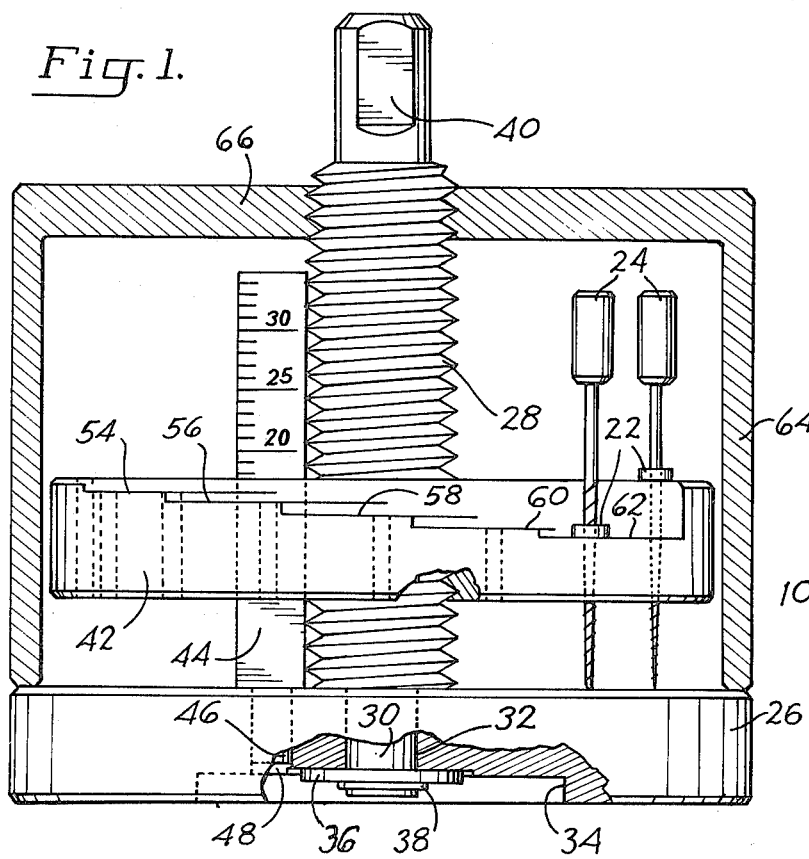
FIG. 1 is a vertical elevation, partly sectioned to disclose details of internal construction, of an endodontic file holder and gauge embodying the features of this invention, the same being shown on an enlarged scale approximately twice actual scale.

Referring now primarily to FIG. 1 of the drawings, the endodontic file holder and gauge of this invention includes a base 26, shown as a circular plate. Although it preferably is made of metal, it may be made of synthetic plastic, ceramic or other suitable material, preferably capable of being subjected to the usual temperatures at which endodontic files are autoclaved.

Supported upon the base and extending upwardly therefrom is an elongated support screw 28 arranged to be rotated about its longitudinal axis relative to the base. Thus, the bottom end portion of the screw illustrated is reduced in diameter to form a journal 30 which extends freely through a central bearing opening 32 in the base. A counterbore 34 in the bottom side of the base receives the projecting end of the journal, which terminates inwardly of the bottom side of the base. The counterbore is enlarged sufficiently to receive a stabilizing washer 36 which is mounted on the projecting portion of the journal and is secured in position releasably by a snap ring 38 engaged removably in an annular groove in the journal.

The screw 28 thus is mounted for rotation about its longitudinal axis relative to the base. The upper end portion of the screw is provided with flattened segments 40, or is otherwise contoured to provide a finger grip by which to facilitate rotation of the screw.

The screw 28 supports a gauge plate 42 in such manner as to effect vertical movement of the gauge plate relative to the base 26 upon rotation of the screw. As illustrated, a central opening in the gauge plate is threaded to match the threads of the screw. Thus, by restraining the gauge plate against rotation while rotating the screw, the gauge plate is moved vertically toward and away from the base.

Means is provided for preventing rotation of the gauge plate while allowing it to move vertically in the direction of the longitudinal axis of the screw. In the embodiment illustrated, an elongated post 44 is secured to and extends upwardly from the base and slidably engages the gauge plate to prevent axial rotation of the latter. As illustrated, the bottom end of the post is provided with a cylindrical mounting section 46 which is secured, as by a press fit, in a vertical opening 48 in the base a spaced distance radially outward from the screw. An opening 50 in the gauge plate freely receives the post upwardly therethrough, whereby the plate is prevented from rotating while being allowed to move vertically relative to the base as the supporting screw 28 is rotated.

The gauge plate is provided with a multiplicity of radially and circumferentially spaced openings 52 each extending vertically therethrough for the free reception of an endodontic file. The bottom end of each file rests upon the upper surface of the base 26, and the upper surface of the gauge plate functions as a gauging surface for abutment by the depth stopper 22 on the file, for establishing the working length of the file. Thus, it will be apparent that the distance between the upper surface of the base 26 and the upper surface of the gauge plate 42 defines the working length of the main group of files.

Accordingly, the post 44 is provided with a graduated scale, preferably marked in millimeters upwardly from the upper surface of the base, so that the scale marking registering with the upper surface of the gauge plate provides a direct indication of the length, in millimeters, of the working length of those files 20 having their gauge stoppers 22 abutting the upper surface of the gauge plate.

As previously explained, the final stages of treatment involves the use of larger size files which decrease progressively in length by one millimeter increments. In the preferred embodiment of the holder and gauge illustrated, the gauge plate 42 is provided with a portion of its circumference stepped downwardly at one millimeter increments to provide a plurality of segments 54,56, 58, 60 and 62, the upper surface of each of which is spaced a distance of one millimeter from its adjacent segment. Each of the segments is provided with a vertical opening 52' for the reception of an endodontic file, the upper surface of the segment serving as a gauging surface for abutment by the depth stopper 22 on the associated file.

In FIG. 1 of the drawings, there is illustrated two files 20. The one on the right is one of the initial group of files to be used and therefore has its associated depth stopper 22 adjusted into abutment with the uppermost, main surface of the gauge plate 42 to provide the maximum working length. The file on the left is associated with the final stepped segment 62 having the lowermost gauging surface. This is the file illustrated in FIG. 3.

Means also is provided for enclosing the assembly of endodontic files 20 and supporting gauge plate 42. In the embodiment illustrated, a hollow cover is provided in the form an annular side wall 64 closed at its upper end by a top wall 66. A central opening in the top wall is threaded to match the threads of the screw 28, whereby the cover is supported by the screw. It is to be noted that the gauge plate 42 is smaller in diameter than the base 26, whereby the peripheral wall 64 of the cover extends downward about the gauge plate for removable abutment against the upper surface of the base. In this position, the interior of the cover is sealed against the entrance of contaminants and thereby affords a sterile atmosphere for the storage of the assembly of files 20.

It is also to be noted that the depth of the peripheral wall 64 of the cover is only slightly greater than the overall length of the files 20. Accordingly, even with the gauge plate 42 moved downward to its lowermost position of adjustment, the files are retained within the openings 52 in the gauge plate even though the holder and gauge assembly is turned upside down. Accordingly, the closed cover insures that the assembly of files will be retained in proper positions within the gauge plate under all conditions of transport.

It will be appreciated that the cover is adjusted to the closed position illustrated in FIG. 1 by rotating it relative to the screw 28 in the direction to move the lower edge of the cover downward into sealing engagement with the upper surface of the base. In similar manner, the cover may be removed by rotating it in the opposite direction to disengage it from the upper end of the screw.

The threaded mounting of the cover also enables the latter to be adjusted to an intermediate position in which the bottom end of the cover is spaced slightly upward from the base and yet is supported on the screw. In this position the assembly, with used files, may be placed in an autoclave for the purpose of cleaning the files while they are retained in position on the gauge plate. After autoclaving, the cover then may be rotated relative to the screw into sealing engagement with the base. The clean files thus are retained in a sterile environment during storage prior to subsequent use.

The endodontic file holder and gauge described hereinbefore is used as follows: Let it be assumed that a plurality of endodontic files are supported in the openings 52 provided in the gauge plate 42. In this regard, the radially inward group of openings may serve to store a number of extra files which duplicate some of the files retained in the radially outward group of openings through the main portion of the plate.

An X-ray having been taken of the tooth 10 to be treated, the full depth of the canal 12 is measured by an appropriate ruler. With the cover removed, the finger grip upper end of the screw 28 is grasped between the fingers and rotated in the direction to move the gauge plate 42 in the direction to bring its upper surface into registry with the scale marking on the post 44 which matches the scale reading found on the ruler.

The files 20 to be utilized in the treatment then are adjusted to proper working length by first adjusting the depth stoppers on the files to shorter than final length, returning the files to the openings 52 and 52' in the gauge plate 42, and then pushing the files downward until their tip ends abut the upper surface of the base 26. The assembly of files thus is ready for use.

As each file has completed its task, it is returned to its opening in the gauge plate. Upon completion of the treatment, the cover is mounted on the screw and rotated relative thereto to bring the bottom edge of the cover to a position spaced slightly above the base. The assembly then is placed in an autoclave for a time sufficient to effect cleaning of the files. Upon removal of the assembly from the autoclave, the cover is rotated downward into sealing engagement with the base and the assembly moved to its place of storage, ready for subsequent use.

From the foregoing, it will be appreciated that the present invention provides an endodontic file holder and gauge which is of simplified construction for economical manufacture, which supports a plurality of files in a manner facilitating their adjustment to desired working lengths, which displays the files for ready access for use, which retains the files for autoclaving and sterile storage and insures against disarrangement of the files during transport.

It will be apparent to those skilled in the art that various changes may be made in the size, shape, type, number and arrangement of parts described hereinafter without departing from the spirit of this invention.

Having thus described my invention and the manner in which it may be used, I claim:

1. An endodontic file holder and gauge, comprising:
   (a) a base,
   (b) an elongated support screw mounted rotatably on the base and extending upwardly therefrom,
   (c) a gauge plate provided with a central threaded hole receiving the threads of the screw, whereby the gauge plate is supported by the screw,
   (d) the gauge plate being provided with a plurality of vertical openings therethrough for the removable reception of endodontic files,
   (e) a portion of the gauge plate being provided with a plurality of downwardly stepped segments providing a plurality of upper surfaces each spaced a different distance downwardly from the upper surface of the remainder of the gauge plate, each stepped segment having a vertical opening therethrough for the removable reception of an endodontic file, and
   (f) stop means interengaging the base and the gauge plate for preventing rotation of the plate while permitting movement of the plate in the longitudinal direction of the screw as the latter is rotated, whereby to vary the distance between the gauge plate and base.

2. An endodontic file holder and gauge, comprising:
   (a) a base,
   (b) an elongated support screw mounted rotatably on the base and extending upwardly therefrom,
   (c) a gauge plate provided with a central threaded hole receiving the threads of the screw, whereby the gauge plate is supported by the screw,
   (d) the gauge plate being provided with a plurality of vertical openings therethrough for the removable reception of endodontic files, and
   (e) stop means interengaging the base and the gauge plate for preventing rotation of the plate while permitting movement of the plate in the longitudinal direction of the screw as the latter is rotated, whereby to vary the distance between the gauge plate and base, the stop means comprising a post extending upwardly from the base and slidably engaging the gauge plate.

3. The endodontic file holder and gauge of claim 2 wherein the post has scale markings thereon registrable with the gauge plate for indicating the vertical spacing between the upper surface of the base and gauge plate.

4. The endodontic file holder and gauge of claim 2 wherein the gauge plate is provided with a vertical opening freely receiving the post therethrough.

5. An endodontic file holder and gauge, comprising:
   (a) a base,
   (b) an elongated support screw mounted rotatably on the base and entending upwardly therefrom,
   (c) a gauge plate provided with a central threaded hole receiving the threads of the screw, whereby the gauge plate is supported by the screw,
   (d) the gauge plate being provided with a plurality of vertical openings therethrough for the removable reception of endodontic files,
   (e) stop means interengaging the base and the gauge plate for preventing rotation of the plate while permitting movement of the plate in the longitudinal direction of the screw as the latter is rotated, whereby to vary the distance between the gauge plate and base, and
   (f) a cover having a top wall and a downwardly extending peripheral wall arranged for removable sealing engagement with the base with the gauge plate confined removably within the cover, the top wall of the cover having a threaded opening removably receiving the thread of the screw, whereby the cover is supported by the screw and is rotatable relative to the screw for adjusting it upwardly from a position of sealing engagement of the bottom end of the peripheral wall with the base to a position of disengagement of the thread in the top wall from the screw.

* * * * *